United States Patent
Cho et al.

(10) Patent No.: US 10,456,362 B2
(45) Date of Patent: *Oct. 29, 2019

(54) STABILIZED PHARMACEUTICAL COMPOSITION AND METHOD FOR PREPARING SAME

(71) Applicant: SAMYANG BIOPHARMACEUTICALS CORPORATION, Seoul (KR)

(72) Inventors: Joong-Woong Cho, Daejeon (KR); Gyeong-Hae Kim, Daejeon (KR); Min-Hyo Seo, Daejeon (KR); Sa-Won Lee, Daejeon (KR)

(73) Assignee: SAMYANG BIOPHARMACEUTICALS CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/561,118

(22) PCT Filed: May 27, 2016

(86) PCT No.: PCT/KR2016/005653
§ 371 (c)(1),
(2) Date: Sep. 25, 2017

(87) PCT Pub. No.: WO2016/190712
PCT Pub. Date: Dec. 1, 2016

(65) Prior Publication Data
US 2018/0125786 A1 May 10, 2018

(30) Foreign Application Priority Data
May 28, 2015 (KR) .......................... 10-2015-0074540

(51) Int. Cl.
| | | |
|---|---|---|
| A61K 47/02 | (2006.01) | |
| A61K 47/18 | (2017.01) | |
| A61K 9/08 | (2006.01) | |
| A61K 31/519 | (2006.01) | |
| A61K 9/00 | (2006.01) | |
| A61P 35/00 | (2006.01) | |
| A61K 9/19 | (2006.01) | |
| A61K 47/20 | (2006.01) | |

(52) U.S. Cl.
CPC .............. *A61K 9/19* (2013.01); *A61K 9/0019* (2013.01); *A61K 9/08* (2013.01); *A61K 31/519* (2013.01); *A61K 47/02* (2013.01); *A61K 47/18* (2013.01); *A61K 47/20* (2013.01); *A61P 35/00* (2018.01)

(58) Field of Classification Search
None
See application file for complete search history.

(56) References Cited

U.S. PATENT DOCUMENTS

2007/0213411 A1* 9/2007 Francis ................ A61K 9/0019
516/53
2011/0201596 A1* 8/2011 Alli ...................... A61K 9/0048
514/214.02

FOREIGN PATENT DOCUMENTS

| CN | 103006584 | 4/2013 |
|---|---|---|
| CN | 103432086 | 12/2013 |
| JP | 2003-521518 | 7/2003 |
| KR | 10-2002-0081293 | 10/2002 |
| KR | 10-1069128 | 9/2011 |
| KR | 10-1260636 | 5/2013 |
| WO | 2001-056575 | 8/2001 |
| WO | 2012-121523 | 9/2012 |
| WO | 2013-179248 | 12/2013 |
| WO | 2014-060962 | 4/2014 |
| WO | 2014-182093 | 11/2014 |
| WO | 2014-198337 | 12/2014 |
| WO | 2015-050230 | 4/2015 |
| WO | 2015-102315 | 7/2015 |

OTHER PUBLICATIONS

English Machine Translation of KR 101260636 [online]. Retrieved on Jun. 30, 2018. Retrieved from the internet: <www.espacenet.com>. (Year: 2018).*
Machine Translation of KR 101069128 [online]. Espacenet [retrieved on Oct. 6, 2019]. Retrieved from the internet: <www.epo.org>. (Year: 2011).*
Yanping Zhang et al., "Physical instability of frozen pemetrexed solutions in PVC bags", The Annals of pharmacotherapy, vol. 40, pp. 1289-1292, Jul./Aug. 2006, Oncology.
"SOP—Freeze-Pump-Thaw Degassing of Liquids", Safety Web, Oregon State University, Department of Chemistry, Standard Operating Procedure: Freeze-Pump-Thaw Degassing of Liquids, Jan. 30, 2018, <URL: http://chemsafety.chem.oregonstate.edu/content/sop-freeze-pump-thaw-degassing-liquids>.
Sarah Millar, "Tips and Tricks for the Lab: Air-Sensitive Techniques (2)", Wiley-VCH Verlag GmbH & Co. KGaA, Weinheim, Jan. 30, 2018, <URL: http://www.chemistryviews.org/details/education/4308331/tips_and_tricks-for_the_lab_air-sensitive_techniques_2.html>.
EPO, a copy of the extended European search report of EP 16800351.5 dated Dec. 7, 2018.

* cited by examiner

*Primary Examiner* — Katherine Peebles
(74) *Attorney, Agent, or Firm* — Lex IP Meister, PLLC

(57) ABSTRACT

Provided are a composition containing an unstable drug against oxidation like pemetrexed with improved stability and a preparation method thereof, by removing oxygen during the preparation. The method is readily applicable for manufacturing by freezing and degassing in a sealed chamber, and can provide formulations with significantly increased stability for the unstable drug against oxidation.

13 Claims, No Drawings

STABILIZED PHARMACEUTICAL COMPOSITION AND METHOD FOR PREPARING SAME

TECHNICAL FIELD

The present disclosure relates to a pharmaceutical composition with improved stability, including pemetrexed or pharmaceutically acceptable salts thereof, and a preparation method thereof.

RELATED ART

Pemetrexed disodium is a new multitargeted antifolate with excellent anti-cancer activity applied to various solid cancers such as non-small cell lung cancer (NSCLC), malignant pleural mesothelioma, breast cancer, colon cancer, uterine cancer, head and neck cancer, and bladder cancer. Alimta (trademark) has been used in the clinical field as a lyophilized injectable formulation. Alimta is administered in combination with cisplatin to a patient with malignant pleural mesothelioma who has not been received chemotherapy and is not eligible for surgery. Since 2007, it has also been used as a single administration to locally advanced breast cancer or NSCLC patients after chemotherapy.

Most lyophilized injectable formulations are currently used by preparing a lyophilized powder due to the instability of a drug in an aqueous solution and reconstituting the powder with physiological saline or water for injection before injection to a patient. However, the reconstitution is a cumbersome process in that a desired amount of saline or water should be weighed and poured into a vial, and has the risk of microbial contamination and a limitation in that the reconstituted formulation must be used within a certain period of time. Further, the lyophilized formulation has a high production cost and a complex manufacturing process due to a long drying cycle during the lyophilization. Therefore, in considering the production cost and user convenience, there is a need for a ready-to-use liquid formulation with stability.

However, pemetrexed is rapidly oxidized in an aqueous solution and as a result, produces various related compounds. For a drug unstable in liquid, a representative method of increasing the stability thereof is to add an antioxidant or to remove dissolved oxygen. As examples of using an antioxidant, WO2001/56575 discloses a liquid formulation including pemetrexed and an antioxidant such as monothioglycerol, L-cysteine, or thioglycolic acid. KR 10-1260636 discloses that acetyl cysteine is used as an antioxidant and citric acid is used as a buffering agent, so as to provide a formulation with increased stability for pemetrexed. WO2012/121523 discloses a preparation method to increase stability by controlling dissolved oxygen concentration (DOC) in an injectable solution to be 1 ppm or lower without using an antioxidant. However, the preparation method disclosed in the document can be carried out in a lab scale but has many difficulties in a commercial scale. Particularly, in the case that water for injection or an aqueous solution, which has been degassed, is dispensed into a glass vial in a commercial scale, it is very difficult to maintain the degassed state. Therefore, the process could prevent oxidation to increase stability without using an antioxidant, but could hardly be scaled up to a commercial manufacturing process.

DISCLOSURE

Technical Problem

In consideration of the problems in the art, one object of the present invention is to provide a pharmaceutical composition with stability in an aqueous solution, and a preparation method thereof, which method can be applied for commercial production in a large scale, by performing all steps in a sealed chamber.

Another object of the present invention is to provide a pharmaceutical composition with improved stability and a preparation method thereof, by removing oxygen.

Still another object of the present invention is to provide a pharmaceutical composition with improved stability including pemetrexed and a preparation method thereof, which method is performed by simply carrying out freezing and degassing in a sealed chamber, instead of preparing the composition from an aqueous solution that has been degassed in a sealed system, thereby obtaining stability of the drug unstable against oxidation as well as being applicable for commercial production in a large scale.

A still further another object of the present invention is to provide a pharmaceutical composition in an aqueous solution storable at room temperature, which has no color changes as well as improved stability, and a preparation method thereof, which method is performed by carrying out freezing and degassing as described above, with addition of an antioxidant.

Technical Solution

To resolve the problems, an embodiment of the present invention provides a method of preparing a pharmaceutical composition, including: (a) freezing a solution including pemetrexed or a pharmaceutically acceptable salt thereof and an aqueous solvent to obtaining a frozen product; and (b) degassing the frozen product under reduced pressure to obtain a degassed and frozen product.

Another embodiment of the present invention provides a pharmaceutical composition including pemetrexed or a pharmaceutically acceptable salt thereof and an aqueous solvent that is frozen and degassed.

The solution of step (a) can be a solution which has not been degassed, and can be frozen at −20° C. or lower.

The solution or pharmaceutical composition of step (a) comprises pemetrexed or a pharmaceutically acceptable salt thereof, at an amount of 5 to 100 mg/ml, preferably 10 to 50 mg/ml, more preferably 20 to 30 mg/ml, as pemetrexed.

The solution or the pharmaceutical composition of step (a) may further comprise at least one selected from the group consisting of pharmaceutically acceptable excipients and pH adjusting agents. For example, the excipient is mannitol, or the pH adjusting agent is hydrochloric acid, sodium hydroxide or a mixture thereof. The excipient may be used in an amount of 0.1 to 10% by weight, preferably 1 to 5% by weight, more preferably 2 to 3% by weight, based on the total weight of the solution or composition. The pH adjusting agent may be used in an amount to adjust the pH of the solution or the composition to be in the range of 6 to 8, preferably 6.5 to 8.0, more preferably 6.6 to 7.8, still more preferably 7.0 to 7.5.

The solution or the pharmaceutical composition of step (a) may further comprise an antioxidant. As the antioxidant, those conventionally used in the art can be used, and examples of antioxidant are monothioglycerol, L-cysteine, thioglycolic acid, ascorbic acid, sodium thiosulfate, butylated hydroxyanisole, propyl gallate, EDTA, L-methionine, L-cystine, sodium sulfite, sodium sulfide, EDTA disodium, citric acid, lipoic acid, dihydrolipoic acid, L-arginine, L-glutathione, L-tryptophan, or a mixture thereof, preferably monothioglycerol, sodium sulfide, acetylcysteine, or a mixture thereof, more preferably, monothioglycerol. The antioxidant may be used at a concentration of 0.01 to 10 mg/ml, preferably 0.1 to 5 mg/ml, or more preferably 1 to 3 mg/ml.

The present invention is characterized in that in step (b), the degassing is performed for the frozen product of the solution containing pemetrexed or a pharmaceutically acceptable salt thereof and an aqueous solvent.

The degassed and frozen product may include a solvent in an amount of 95 to 100 parts by weight, with respect to 100 parts by weight of the solvent contained in the solution of step (a), and the degassing may be performed to 1.5 ppm or less of DOC in step (b).

Preferably, the freezing, the degassing, and optionally a sealing may be carried out in a sealed chamber. The method may further include thawing the degassed and frozen product after step (b) or the sealing step. The pressure of step (b) may be 2,000 mTorr or lower.

An embodiment of the present invention relates to a method of reducing a dissolved oxygen concentration of a pharmaceutical composition, including: (a) freezing a composition containing an aqueous solvent and pemetrexed or a pharmaceutically acceptable salt thereof to produce a frozen product; and (b) degassing the frozen product under reduced pressure to obtain a degassed and frozen product.

Another embodiment of the present invention relates to a method of stabilizing a pharmaceutical composition, including: (a) freezing a composition containing an aqueous solvent and pemetrexed or a pharmaceutically acceptable salt thereof to produce a frozen product; and (b) degassing the frozen product under reduced pressure to obtain a degassed and frozen product.

A preferred embodiment of the present invention relates to a method of increasing stability of a drug unstable against oxidation by removing dissolved oxygen in an aqueous solution, including: (a) freezing a composition containing an aqueous solvent and pemetrexed or a pharmaceutically acceptable salt thereof to produce a frozen product; and (b) degassing the frozen product under reduced pressure to obtain a degassed and frozen product, in a sealed chamber, or (a) freezing a composition containing an aqueous solvent and pemetrexed or a pharmaceutically acceptable salt thereof to produce a frozen product, (b) degassing the frozen product under reduced pressure to obtain a degassed and frozen product, and (c) sealing the degassed and frozen product, in a sealed chamber.

In another embodiment, the solution of step (a) can further comprise an antioxidant. The antioxidant can be any conventional one and the examples are described above.

The present invention employs degassing for increasing stability of a drug unstable against oxidation, because all processes are carried out in a sealed chamber, it can be easily performed in a sterile chamber without contamination. Therefore, the degassing step of the present invention has various advantages in time, convenience, and production yield, compared to the prior degassing step.

Further, the present invention employs an antioxidant in addition to the freezing and degassing, thereby efficiently providing a pharmaceutical composition in an aqueous solution storable at room temperature, which has no color changes as well as improved stability.

Advantageous Effect

The preparation method of the present invention is suitable for a large-scale production, and is a simple method performed in a sterile chamber without contamination, because the freezing, the degassing, and the sealing can be performed continuously in a sealed chamber. The method is efficient in aspects of time, convenience, and production yield, compared to the prior degassing method.

DETAILED DESCRIPTION

The present invention will be explained in more detail.

An embodiment of the present invention provides a method of preparing a pharmaceutical composition with excellent stability on a commercial scale, including: freezing a composition containing an aqueous solvent and pemetrexed or a pharmaceutically acceptable salt thereof to produce a frozen product; and (b) degassing the frozen product under reduced pressure, e.g. in vacuum, to obtain a degassed and frozen product.

Another embodiment of present invention relates to a pharmaceutical composition including an aqueous solvent and pemetrexed, or a pharmaceutically acceptable salt thereof that is frozen and degassed. The pharmaceutical composition may be thawed and used as a liquid parenteral formulation, specifically a liquid injectable formulation.

In step (a), a solution including pemetrexed or a pharmaceutically acceptable salt and an aqueous solvent can be prepared and frozen to produce a frozen product. In addition, the solution can be dispensed into a filling container before the freezing step. The solution of step (a) is poured into a container such as an ampoule or a vial, and then the freezing, the degassing, and the sealing can be carried out continuously in a sealed chamber, thereby making the method be advantageous in maintaining the degassed state during large-scale production.

In the present invention, the term "pemetrexed" is a 5-substituted pyrrolo[2,3-d]pyrimidine as represented by Chemical Formula 1, and is a multitargeted antifolate with anti-cancer activity applied to various solid cancers such as non-small cell lung cancer (NSCLC), malignant pleural mesothelioma, and the like.

Chemical Formula 1

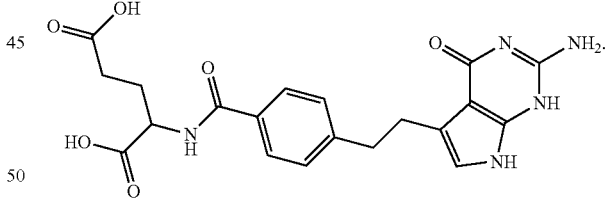

In the present invention, the term "pharmaceutically acceptable salts" refers to salts prepared according to conventional methods in the art. Specifically, the pharmaceutically acceptable salts include salts derived from inorganic acids, organic acids, and bases that are pharmaceutically acceptable, but are not limited thereto. Examples of suitable acids are hydrochloric acid, bromic acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzene sulfonic acid, and the like. Examples of suitable bases include alkali metals such as sodium or potassium, and alkaline earth metals such as magnesium, but are not limited to thereto. In particular, a pharmaceutically acceptable salt of pemetrexed can be pemetrexed disodium salt, but is not limited thereto.

In the present invention, the term "pemetrexed or pharmaceutically acceptable salts thereof" includes hydrates of pemetrexed or pharmaceutically acceptable salts thereof, and includes any types of hydrates, for example, 2.5-hydrate, 7-hydrate, etc., but are not limited thereto.

The aqueous solvent may be water or a buffer solution, for example, water for injection or physiological saline.

The pharmaceutical composition according to the present invention may include one or more selected from the group consisting of a pharmaceutically acceptable excipient and a pH adjusting agent, and for example, the excipient may be mannitol, and the pH adjusting agent may be hydrochloric acid, sodium hydroxide, or a mixture thereof. The excipient and the pH adjusting agent may be added to the solution of step (a).

The solution or pharmaceutical composition of step (a) may further comprise an antioxidant. As the antioxidant, those conventionally used in the art can be used, and examples of antioxidant are monothioglycerol, L-cysteine, thioglycolic acid, ascorbic acid, sodium thiosulfate, butylated hydroxyanisole, propyl gallate, EDTA, L-methionine, L-cystine, sodium sulfite, sodium sulfide, EDTA disodium, citric acid, lipoic acid, dihydrolipoic acid, L-arginine, L-glutathione, L-tryptophan, or a mixture thereof, preferably monothioglycerol, sodium sulfide, acetylcysteine, or a mixture thereof, more preferably, monothioglycerol. The antioxidant may be used at a concentration of 0.01 to 10 mg/ml, preferably 0.1 to 5 mg/ml, or more preferably 1 to 3 mg/ml. For example, the monothioglycerol may be used in an amount of 0.01 to 10 mg/ml, preferably more than 0.1 to 5 mg/ml, more preferably 0.2 to 3 mg/ml, such as 0.24 to 3 mg/ml. It can be used at a concentration of 1 to 3 mg/ml.

A solution or a solvent of step (a) may be one that has not been degassed. In order to control the dissolved oxygen concentration in liquid formulations, the prior-art method should include a step of controlling the dissolved oxygen concentration for an aqueous solvent itself or a solution containing a drug dissolved in the aqueous solvent. However, the present invention does not require the step of degassing or controlling the dissolved oxygen concentration for the aqueous solvent itself or the solution containing a drug dissolved in the aqueous solvent, because the degassing step is performed after a freezing step. According to the present invention, a highly stable liquid formulation can be easily and simply prepared.

The freezing of the solution in step (a) can be performed at a temperature of −20° C. or lower, preferably −30° C. or lower, for example −50° C. to −20° C., or −50° C. to −30° C., particularly −40° C. Any freezing method of liquid formulations can be applied for the present invention.

The degassed and frozen product of step (b) may include a solvent in an amount of 95 to 100 parts by weight or more, preferably 98 to 100 parts by weight, with respect to 100 parts by weight of the solvent contained in the solution of step (a). The most solvent in the degassed and frozen product may be maintained after degassing the frozen product. Thus, the degassed and frozen product may be a liquid composition when thawed, and may be used directly without a reconstitution step. Unlike the conventional lyophilized powder preparations, the pharmaceutical composition is prepared by performing a degassing step to control the dissolved oxygen concentration in step (b) but not a drying step to remove the solvent, thereby stabilizing pemetrexed or pharmaceutically acceptable salts unstable against oxidation.

The dissolved oxygen concentration of the degassed and frozen product obtained in step (b) or the thawed product thereafter may be 1.5 ppm or less. The stability of oxygen-labile pemetrexed or a pharmaceutically acceptable salt can be obtained by reducing the dissolved oxygen concentration in the pharmaceutical composition by performing the degassing step.

In another embodiment of the present invention, the freezing and degassing steps, and preferably a sealing step, in the method of preparing the pharmaceutical composition, can be carried out in a sealed chamber. Specifically, the solution of step (a) may be frozen at a temperature of −20° C. or lower, and the frozen product may be degassed under reduced pressure and sealed immediately thereafter. Therefore, the freezing, the degassing, and the sealing are performed continuously in one chamber.

In an embodiment of present invention, the method can further include filling nitrogen into the container filled with the composition, before the sealing step and after the freezing of step (a) and the degassing of step (b). In order to prevent the occurrence of air backflow due to negative pressure caused by the vacuum in the head space of the filled container, the negative pressure is reduced by filling nitrogen into the container filled with the composition before the sealing step and after the degassing step, so as to largely decrease the risk of air backflow. Specifically, the method can further include de-vacuumizing by filling nitrogen before sealing the container with a rubber stopper. The dissolved oxygen is not sufficiently removed or air can be penetrated even through small pores if the negative pressure is maintained in the vial, although the sealing step after degassing and the de-vacuuming step are performed. Therefore, the nitrogen filling before the sealing step can significantly decrease the negative pressure inside the vial, thereby reducing the risk.

In general, the vacuuming in a liquid state causes boiling-over of the liquid by vapor pressure, but the vacuuming can remove gas with a lower freezing point than an aqueous solution without causing loss of components and contents of the composition.

Herein, the term "degassing" refers to removal of gas molecules from a solid or liquid. The basic principle of removing the gas molecules is based on Henry's law and Dalton's law on partial pressure. Henry's law states that the amount of dissolved gas in solution is proportional to its partial pressure in a gas contacting the solution. The decrease of pressure in the gas contacting the solution, e.g. vacuum, causes the gas molecules to be discharged from the liquid.

Alternatively, by using the principle that the saturation degree of a dissolved gas depends on the temperature of a liquid, heating of the liquid causes the gas molecules to be discharged from the liquid. The method of liquid heating requires energy consumption for heating the liquid, and cannot be suitable for medicines because of denaturation or concentration change of heat-labile drugs or excipients. Various degassing methods such as membrane degassing and catalytic resin degassing are used as well, but cannot be applied to the production due to many difficulties such as a complex production process. Such degassing step with vacuum or reduced pressure can block the oxidative reaction by significantly decreasing the dissolved oxygen concentration in an aqueous solution.

The degassing of step (b) can be carried out under the pressure of 2,000 mTorr or lower, preferably 1,000 mTorr or lower, or more preferably 500 mTorr or lower, for example 300 mTorr or lower. The pressure may be 0 mTorr or higher, or preferably 5 mTorr or higher, for example 100 mTorr or higher. For example, the degassing is performed under the pressure of 0 to 2,000 mTorr, particularly 5 to 1,000 mTorr, preferably 100 to 500 mTorr. The degassing is performed to maintain the desired degree of vacuum for a predetermined period of time after achieving the desired degree of vacuum, thereby removing oxygen or oxygen-containing gas from the frozen product.

The present invention is distinguishable from a typical freeze-drying process in that the vacuum is released prior to occurrence of drying, when the desired vacuum state is achieved by reducing the pressure. This is because the concentration of the active ingredient increases due to the reduction of the solvent as the drying proceeds. To prevent the drying in advance, the degree of vacuum after achieving the desired degree of vacuum is maintained for 12 hours or shorter, more preferably 10 hours or shorter, or most preferably 6 hours or shorter. For example, the sealing and/or the vacuum relief may be performed immediately (0 hour) after achieving the desired degree of reduced pressure.

The solvent in the degassed and frozen composition or the thawed liquid composition may be ideally maintained in an amount of 100 parts by weight, preferably 95 to 100 parts by weight, or more preferably 98 to 100 parts by weight, with respect to 100 parts by weight of the solvent in the solution prior to the degassing step.

In addition, the thawing step can be carried out by increasing the temperature in the sealed chamber, or outside of the sealed chamber. Preferably, it is avoided to take out the vial from the sealed chamber at a too low temperature, because moisture formed on the surface of the vial may make aluminum capping troublesome.

Furthermore, the pharmaceutical composition obtained by performing the freezing and degassing can be sterilized according to any method such as sterilized filtration and/or heat sterilization. In addition, the aqueous solvent or the solution in step (a) of the present invention can be sterilized according to any method such as sterilized filtration and/or heat sterilization.

DETAILED DESCRIPTION OF THE EMBODIMENTS

The present invention will be described in more detail with reference to the following examples. However, these examples are for illustrative purposes only, and the invention is not intended to be limited by these examples.

[Examples 1 to 5] Preparation of Liquid Formulations with Various Vacuum Degrees (1) Preparation of Mixed Solution Filled in Vials 48.3 g (40 g as pemetrexed) of pemetrexed disodium 2.5-hydrate was dissolved completely in 1500 ml of water for injection and 40 g of mannitol was added thereto and completely dissolved. To the obtained solution was added 0.1N HCl to adjust the pH to 7.3, and water for injection was added thereto to adjust a total weight of the mixed solution to 1,600 g. DOC of the mixed solution was about 7.0 ppm. The mixed solution was filtered with a sterile filter, filled into 5 ml vials to be 4 ml per vial in a clean bench, and the vials were sealed with rubber stoppers to obtain the mixed solution filled in the vials.

(2) Freezing and Degassing

The glass vials filled with the mixed solution were introduced into a sealed chamber with their rubber stopper slightly opened, and the solution was frozen at −40° C. for 1 hour. After confirming that the solution was completely frozen, vacuumization began by operating a vacuum pump in the sealed chamber, while maintaining the temperature of −40° C. The vacuum degree was controlled as shown in Table 1, and the vacuum pump was stopped immediately after the desired degree of vacuum reached and then the vials were sealed with rubber stoppers. The vacuum was released after confirming that the vials were sealed. The glass vials were taken out from the sealed chamber, and thawed and capped with aluminum caps. The DOC of the degassed and frozen formulation is shown in Table 1.

DOC was measured with an YSI 550A DOC analyzer with agitation in a glove box filled with nitrogen. The properties of the thawed solution are shown in Table 1.

TABLE 1

| | Concentration of active ingredient (mg/ml) | Vacuum degree (Torr) | DOC (ppm) | pH |
|---|---|---|---|---|
| Example 1 | 25 | 2 | 1.5 | 7.3 |
| Example 2 | 25 | 1 | 1.1 | 7.3 |
| Example 3 | 25 | 0.5 | 0.7 | 7.3 |
| Example 4 | 25 | 0.3 | 0.5 | 7.3 |
| Example 5 | 25 | 0.1 | 0.5 | 7.3 |

[Example 6] Preparation of Liquid Formulations by Freezing, Degassing, and Nitrogen-Filling The glass vials filled with the mixed solution were obtained according to the same method of Example 1. The glass vials filled with the mixed solution were introduced into a sealed chamber with their rubber stopper slightly opened, and the solution was frozen at −40° C. for 1 hour. After confirming that the solution was completely frozen, the vacuumization began by operating a vacuum pump in the sealed chamber, while maintaining the temperature of −40° C. The vacuum pump was stopped immediately after the degree of vacuum reached 300 mTorr, and the vials were filled with nitrogen and sealed with rubber stoppers. The vacuum was released after confirming that the vials were sealed. The glass vials were taken out from the sealed chamber, and were thawed and capped with aluminum caps. The DOC of the degassed and frozen formulation was about 0.5 ppm.

[Examples 7 to 9] Preparation of Liquid Formulations by Adding an Antioxidant, and Freezing and Degassing 48.3 g (40 g as pemetrexed) of pemetrexed disodium 2.5-hydrate was dissolved completely in 1500 ml of water for injection and 40 g of mannitol was added thereto and completely dissolved. To the obtained solution was added the antioxidant as shown in the following Table 2 and was added 0.1 N HCl or 0.1 to 1 N NaOH to adjust the pH to 7.3, and water for injection was added thereto to adjust a total weight of the mixed solution to 1,600 g. DOC of the mixed solution was about 7.0 ppm. The mixed solution was filtered with a sterile filter, filled into 5 ml vials to be 4 ml per vial in a clean bench, and the vials were sealed with rubber stoppers to obtain the mixed solution filled in the vials.

The glass vials filled with the mixed solution were introduced into a sealed chamber with their rubber stopper slightly opened, and the solution was frozen at −40° C. for 1 hour. After confirming that the solution was completely frozen, the vacuumization began by operating a vacuum pump in the sealed chamber, while maintaining the temperature of −40° C. The vacuum pump was stopped immediately, when the vacuum degree reached 200 mTorr, and then the vials were sealed with rubber stoppers. After confirming that the vials were sealed, the glass vials were taken out from the sealed chamber, and thawed and capped with aluminum caps. The DOC of the degassed and frozen formulation was 0.5 ppm.

TABLE 2

| | Concentration of active ingredient (mg/ml) | Kind of antioxidant | Concentration of antioxidant | pH |
|---|---|---|---|---|
| Example 7 | 25.0 | Monothioglycerol | 2.4 | 7.3 |
| Example 8 | 25.0 | Sodium sulfide | $2.4 \times 10^{-3}$ | 7.4 |
| Example 9 | 25.0 | Acetylcysteine | 1.5 | 7.3 |

[Examples 10 to 15] Preparation of Liquid Formulations by Freezing and Degassing to Test the Effect of Antioxidant Concentration and the Scale-Up 241.5 g (200 g as pemetrexed) of pemetrexed disodium 2.5-hydrate was dissolved completely in 7500 ml of water for injection and 200 g of mannitol was added thereto and completely dissolved. To the obtained solution was added the antioxidant at various concentrations as shown in the following Table 3 and was added 0.1 N HCl or 0.1 to 1 N NaOH to adjust the pH to 7.3, and water for injection was added thereto to adjust a total weight of the mixed solution to 8,000 g. DOC of the mixed solution was about 7.0 ppm. The mixed solution was filtered with a sterile filter, filled into 5 ml vials to be 4 ml per vial in a clean bench, and the vials were sealed with rubber stoppers to obtain the mixed solution filled in the vials.

The glass vials filled with the mixed solution were introduced into a sealed chamber with their rubber stopper slightly opened, and the solution was frozen at −40° C. for 3 hours. After confirming that the solution was completely frozen, the vacuumization began by operating a vacuum pump in the sealed chamber, while maintaining the temperature of −40° C. The vacuum pump was stopped immediately, when the vacuum degree reached 200 mTorr, and then the vials were sealed with rubber stoppers. After confirming that the vials were sealed, the glass vials were taken out from the sealed chamber, and thawed and capped with aluminum caps. The DOC of the degassed and frozen formulation was 0.5 ppm.

TABLE 3

| | Concentration of active ingredient (mg/ml) | kind of antioxidant | concentration of antioxidant | pH |
|---|---|---|---|---|
| Example 10 | 25.0 | Monothioglycerol | 0 | 7.3 |
| Example 11 | 25.0 | Monothioglycerol | 2.4 | 7.3 |
| Example 12 | 25.0 | Monothioglycerol | 1.2 | 7.3 |
| Example 13 | 25.0 | Monothioglycerol | 0.6 | 7.3 |
| Example 14 | 25.0 | Monothioglycerol | 0.24 | 7.3 |
| Example 15 | 25.0 | Monothioglycerol | 0.1 | 7.3 |

[Comparative Example 1] Preparation of Liquid Formulations without Freezing and Degassing The glass vials filled with the mixed solution were obtained according to the same method of Example 1. The vials were capped with aluminum caps. The DOC of the formulation was about 7.0 ppm.

[Comparative Example 2] Preparation of Liquid Formulations without Freezing and Degassing, but with Nitrogen-Filling The glass vials filled with the mixed solution were obtained according to the same method of Example 1. The vials were filled with nitrogen and sealed with rubber stoppers and capped with aluminum caps. The DOC of the formulation was about 7.0 ppm.

[Comparative Examples 3 to 5] Preparation of Liquid Formulations without Freezing and Degassing, but with the Addition of Antioxidant The glass vials filled with the mixed solution were obtained according to the same method of Examples 7 to 9. The vials were sealed with rubber stoppers and capped with aluminum caps. The DOC of the formulation was about 7.0 ppm.

[Test Example 1] Accelerated Stability Test

The stability of formulations obtained in Examples 1 to 6 and Examples 7 to 9 and Comparative Examples 1 to 2 and 3-5 was tested under an accelerated condition (40° C./75% RH). The stability test was performed by analyzing the appearance, pH, drug content, and amount of related compounds (unidentified impurities) of the aqueous solution with HPLC.

A. HPLC Condition for Drug Content Analysis a. column: Zorbax SB-C8, 4.6 mm×150 mm, 3.5 μm, or column similar thereto b. detector: UV spectrophotometer (measuring wavelength: 285 nm)

c. injection volume: 20 μl d. flow rate: 1.0 mL/min e. column temperature: 30° C.

f. mobile phase: acetate buffer solution:acetonitrile=(89:11) (v/v %)

* acetate buffer solution (30 mM, pH 5.3±1): Acetic anhydride was added to distilled water at a volume of 1.7 mL per 1 L of distilled water, and then, they were mixed together well, and a pH of the mixture was adjusted to 5.3±0.1 with the addition of 50% NaOH, and the mixture was filtered if necessary.

B. HPLC Condition for Related Compound Analysis a. column: Zorbax SB-C8, 4.6 mm×150 mm, 3.5 μm, or column similar thereto b. detector: UV spectrophotometer (measuring wavelength: 250 nm)

c. injection volume: 20 μl d. flow rate: 1.0 mL/min e. column temperature: 25° C.

f. auto-injector temperature: 2 to 8° C.

g. mobile phase: gradient elution

TABLE 4

| Time (min) | Mobile phase A (%) | Mobile phase B (%) |
|---|---|---|
| 0 | 100 | 0 |
| 45 | 0 | 100 |
| 47 | 100 | 0 |
| 60 | 100 | 0 |

Mobile phase A: formate buffer solution:acetonitrile=95:5 (v/v)

Mobile phase B: formate buffer solution:acetonitrile=70:30 (v/v)

Formate buffer solution: 2.9 g of ammonium formate was dissolved in 2 L of distilled water, and a pH of the solution was adjusted to 3.5±0.1 with formic acid.

As shown above, the accelerated stability tests for the formulations of the examples and comparative examples (40° C./75% RH) were carried out for 12 weeks, and the results are shown in Table 5. The qualification standards were pH of 6.6 to 7.8, drug content of 95 to 105%, 1.5% or lower of total related compounds, and 0.2% or lower of individual related compound.

TABLE 5

| | Time (week) | Appearance | pH | Drug content (%) | Total related compounds (%) | Individual related compound (%) |
|---|---|---|---|---|---|---|
| Example 1 | 0 | colorless | 7.3 | 103.2 | 0.04 | 0.04 |
| | 1 | slightly light yellow | 7.3 | 99.5 | 0.65 | 0.48 |
| | 2 | light yellow | 7.3 | 91.7 | 2.15 | 0.99 |
| | 3 | yellow | 7.2 | 88.1 | 4.88 | 2.11 |
| | 4 | yellow | 7.1 | 84.7 | 7.66 | 3.77 |
| | 8 | yellow | 7.1 | 82.3 | 12.60 | 5.52 |
| | 12 | dark yellow | 7.0 | 74.0 | 15.33 | 6.89 |
| Example 2 | 0 | colorless | 7.3 | 102.4 | 0.04 | 0.04 |
| | 1 | slightly light yellow | 7.3 | 100.3 | 0.07 | 0.05 |
| | 2 | slightly light yellow | 7.2 | 99.1 | 0.15 | 0.10 |
| | 3 | slightly light yellow | 7.3 | 99.2 | 0.96 | 0.46 |
| | 4 | light yellow | 7.2 | 98.2 | 1.25 | 0.56 |
| | 8 | light yellow | 7.2 | 96.7 | 2.33 | 0.96 |
| | 12 | yellow | 7.1 | 95.3 | 3.05 | 1.38 |
| Example 3 | 0 | colorless | 7.3 | 102.1 | 0.04 | 0.04 |
| | 1 | slightly light yellow | 7.3 | 101.4 | 0.05 | 0.05 |
| | 2 | slightly light yellow | 7.3 | 102.5 | 0.06 | 0.06 |
| | 3 | slightly light yellow | 7.3 | 101.8 | 0.09 | 0.06 |
| | 4 | slightly light yellow | 7.2 | 101.4 | 0.12 | 0.07 |
| | 8 | slightly light yellow | 7.2 | 100.1 | 0.16 | 0.10 |
| | 12 | slightly light yellow | 7.2 | 100.6 | 0.21 | 0.12 |
| Example 4 | 0 | colorless | 7.3 | 103.3 | 0.05 | 0.05 |
| | 1 | colorless | 7.3 | 103.3 | 0.05 | 0.05 |
| | 2 | slightly light yellow | 7.3 | 103.0 | 0.06 | 0.05 |
| | 3 | slightly light yellow | 7.3 | 102.5 | 0.06 | 0.05 |
| | 4 | slightly light yellow | 7.3 | 102.6 | 0.11 | 0.06 |
| | 8 | slightly light yellow | 7.1 | 101.1 | 0.12 | 0.07 |
| | 12 | slightly light yellow | 7.2 | 101.6 | 0.15 | 0.08 |
| Example 5 | 0 | colorless | 7.3 | 102.7 | 0.05 | 0.05 |
| | 1 | colorless | 7.3 | 103.4 | 0.05 | 0.05 |
| | 2 | slightly light yellow | 7.3 | 102.1 | 0.05 | 0.05 |
| | 3 | slightly light yellow | 7.2 | 102.2 | 0.06 | 0.06 |
| | 4 | slightly light yellow | 7.2 | 102.0 | 0.10 | 0.06 |
| | 8 | slightly light yellow | 7.2 | 101.7 | 0.13 | 0.07 |
| | 12 | slightly light yellow | 7.2 | 101.5 | 0.16 | 0.09 |
| Example 6 | 0 | colorless | 7.3 | 103.1 | 0.05 | 0.05 |
| | 1 | colorless | 7.3 | 102.4 | 0.05 | 0.05 |
| | 2 | slightly light yellow | 7.2 | 102.1 | 0.05 | 0.05 |
| | 3 | slightly light yellow | 7.3 | 101.1 | 0.06 | 0.06 |
| | 4 | slightly light yellow | 7.2 | 101.8 | 0.10 | 0.06 |
| | 8 | slightly light yellow | 7.1 | 102.1 | 0.12 | 0.07 |
| | 12 | slightly light yellow | 7.2 | 101.6 | 0.14 | 0.08 |
| Comparative Example 1 | 0 | colorless | 7.3 | 103.5 | 0.05 | 0.05 |
| | 1 | slightly light yellow | 7.2 | 97.5 | 0.90 | 0.52 |
| | 2 | light yellow | 7.2 | 91.0 | 3.05 | 1.33 |
| | 3 | yellow | 7.1 | 84.1 | 9.09 | 4.84 |
| | 4 | yellow | 7.1 | 78.2 | 11.72 | 5.42 |
| | 8 | dark yellow | 7.0 | 71.5 | 16.20 | 6.10 |
| | 12 | dark yellow | 6.9 | 61.9 | 18.56 | 7.14 |

TABLE 5-continued

|  | Time (week) | Appearance | pH | Drug content (%) | Total related compounds (%) | Individual related compound (%) |
|---|---|---|---|---|---|---|
| Comparative Example 2 | 0 | colorless | 7.3 | 102.9 | 0.05 | 0.05 |
|  | 1 | slightly light yellow | 7.3 | 99.1 | 0.76 | 0.53 |
|  | 2 | light yellow | 7.2 | 95.7 | 2.52 | 1.11 |
|  | 3 | yellow | 7.2 | 82.2 | 8.09 | 2.84 |
|  | 4 | yellow | 7.1 | 79.2 | 12.72 | 4.29 |
|  | 8 | dark yellow | 7.1 | 72.8 | 15.01 | 6.00 |
|  | 12 | dark yellow | 7.0 | 66.5 | 17.56 | 6.84 |

As a result of tests, the formulations of Examples 3 to 6 showed similar test results, and it was presumed that the degassing was achieved in a similar level under the vacuum degrees of 500 mTorr or lower. The formulations of comparative examples without degassing showed significantly lower stability irrespective of nitrogen-filling. This shows that the process of removing the dissolved oxygen by degassing significantly improves the stability of pemetrexed.

TABLE 6

|  | Time (week) | Appearance | pH | Drug content (%) | Total related compounds (%) | Individual related compound (%) |
|---|---|---|---|---|---|---|
| Example 7 | 0 | colorless | 7.3 | 101.7 | 0.10 | 0.05 |
|  | 1 | colorless | 7.3 | 101.5 | 0.10 | 0.07 |
|  | 2 | colorless | 7.3 | 100.9 | 0.16 | 0.08 |
|  | 3 | colorless | 7.2 | 101.0 | 0.19 | 0.08 |
|  | 4 | colorless | 7.2 | 100.5 | 0.21 | 0.09 |
|  | 8 | colorless | 7.2 | 101.0 | 0.28 | 0.10 |
|  | 12 | colorless | 7.1 | 100.3 | 0.32 | 0.11 |
| Example 8 | 0 | colorless | 7.4 | 102.3 | 0.08 | 0.04 |
|  | 1 | colorless | 7.4 | 102.0 | 0.05 | 0.05 |
|  | 2 | slightly light yellow | 7.3 | 101.1 | 0.08 | 0.08 |
|  | 3 | slightly light yellow | 7.3 | 101.5 | 0.08 | 0.08 |
|  | 4 | slightly light yellow | 7.3 | 101.4 | 0.09 | 0.09 |
|  | 8 | slightly light yellow | 7.3 | 101.0 | 0.16 | 0.10 |
|  | 12 | light yellow | 7.2 | 101.4 | 0.26 | 0.11 |
| Example 9 | 0 | colorless | 7.3 | 101.9 | 0.14 | 0.05 |
|  | 1 | colorless | 7.3 | 102.3 | 0.18 | 0.07 |
|  | 2 | colorless | 7.2 | 102.0 | 0.21 | 0.08 |
|  | 3 | colorless | 7.2 | 101.7 | 0.24 | 0.09 |
|  | 4 | colorless | 7.2 | 101.8 | 0.31 | 0.09 |
|  | 8 | colorless | 7.1 | 101.4 | 0.40 | 0.11 |
|  | 12 | colorless | 7.1 | 101.1 | 0.47 | 0.14 |
| Comparative Example 3 | 0 | colorless | 7.3 | 102.5 | 0.13 | 0.05 |
|  | 1 | light yellow | 7.3 | 101.0 | 0.45 | 0.17 |
|  | 2 | light yellow | 7.2 | 98.1 | 1.20 | 0.35 |
|  | 3 | yellow | 7.2 | 92.9 | 2.20 | 0.51 |
|  | 4 | yellow | 7.1 | 86.3 | 6.48 | 1.28 |
|  | 8 | dark yellow | 6.9 | 79.6 | 11.85 | 2.66 |
|  | 12 | dark yellow | 6.8 | 71.1 | 19.33 | 5.45 |
| Comparative Example 4 | 0 | colorless | 7.4 | 102.9 | 0.08 | 0.04 |
|  | 1 | slightly light yellow | 7.3 | 99.8 | 0.76 | 0.22 |
|  | 2 | light yellow | 7.1 | 95.7 | 2.22 | 1.01 |
|  | 3 | yellow | 7.0 | 88.2 | 7.09 | 2.85 |
|  | 4 | yellow | 7.0 | 79.2 | 12.62 | 3.66 |
|  | 8 | dark yellow | 6.9 | 72.8 | 18.15 | 5.12 |
|  | 12 | dark yellow | 6.7 | 63.5 | 27.50 | 6.98 |
| Comparative Example 5 | 0 | colorless | 7.3 | 102.8 | 0.15 | 0.05 |
|  | 1 | light yellow | 7.2 | 100.7 | 0.96 | 0.53 |
|  | 2 | light yellow | 7.2 | 96.5 | 3.52 | 1.15 |
|  | 3 | yellow | 7.1 | 90.2 | 7.69 | 2.86 |
|  | 4 | yellow | 6.9 | 75.2 | 10.02 | 4.01 |
|  | 8 | dark yellow | 6.8 | 69.1 | 11.51 | 5.40 |
|  | 12 | dark yellow | 6.6 | 61.2 | 13.65 | 6.84 |

As a result of measurement, Examples 7 to 9 exhibited almost the same results in the change of the content and the formation of related compounds, and showed good stability below the standard of the content change and formation of related compounds. In the consideration of appearance as well, Examples 7 and 9 showed high stability. However, referring to Comparative Examples 3 to 5, in which the formulations were prepared with using antioxidants but not subjected to freezing and degassing, the formulations with antioxidants but not frozen and degassed showed very low stability irrespective of kinds of antioxidants. This shows that the process of removing dissolved oxygen by vacuum degassing is an essential process even if an antioxidant is used.

[Test Example 2] Stress Stability Test

The stability of formulations obtained in Examples 5, and 7-9 and Comparative Examples 4 to 5 was tested under a stressed condition (60° C./80% RH) for 4 weeks. The stability test results are shown in Table 7.

(1.5% or lower), and individual related compound (0.2% or lower) satisfying the qualification standards. However, the formulation of Comparative Example 1 not vacuum degassed showed the drug content and related compounds deviated from the qualification standards and turned dark brown only in 1 week, which indicated the considerable occurrence of oxidation.

Examples 7 and 9 using an antioxidant and subjected to vacuum degassing showed good stability in terms of the drug content and related compounds like Example 5 only subjected to vacuum degassing, but showed an outstanding effect in terms of color changes. Referring to Example 8, sodium sulfide had less effect in terms of color changes than other antioxidants. However, as shown in Comparative Examples 3 to 5, when only antioxidant is used without vacuum degassing, not only color changes but also changes in the drug content and related compounds were large, as in Comparative Example 1, which indicates that was not effective for stabilizing the drug. Based on the results, the formulation having greatly improved stability through the

TABLE 7

| Item | Time (week) | Appearance | pH | Drug content (%) | Total related compounds (%) | Individual related compound (%) |
|---|---|---|---|---|---|---|
| Example 5 | 0 | colorless | 7.2 | 102.1 | 0.05 | 0.05 |
|  | 1 | colorless | 7.2 | 101.2 | 0.07 | 0.05 |
|  | 2 | slightly light yellow | 7.2 | 101.6 | 0.16 | 0.07 |
|  | 3 | slightly light yellow | 7.1 | 100.5 | 0.22 | 0.09 |
|  | 4 | light yellow | 7.1 | 101.0 | 0.29 | 0.12 |
| Example 7 | 0 | colorless | 7.3 | 102.5 | 0.10 | 0.05 |
|  | 1 | colorless | 7.2 | 101.9 | 0.23 | 0.08 |
|  | 2 | colorless | 7.2 | 101.6 | 0.31 | 0.08 |
|  | 3 | colorless | 7.1 | 101.5 | 0.35 | 0.09 |
|  | 4 | colorless | 7.1 | 101.5 | 0.36 | 0.09 |
| Example 8 | 0 | colorless | 7.4 | 102.0 | 0.04 | 0.04 |
|  | 1 | colorless | 7.3 | 101.5 | 0.09 | 0.05 |
|  | 2 | slightly light yellow | 7.2 | 101.1 | 0.20 | 0.08 |
|  | 3 | slightly light yellow | 7.2 | 100.9 | 0.28 | 0.10 |
|  | 4 | light yellow | 7.1 | 101.0 | 0.34 | 0.12 |
| Example 9 | 0 | colorless | 7.3 | 101.5 | 0.14 | 0.07 |
|  | 1 | colorless | 7.2 | 101.2 | 0.30 | 0.08 |
|  | 2 | colorless | 7.2 | 101.3 | 0.40 | 0.09 |
|  | 3 | colorless | 7.2 | 100.5 | 0.44 | 0.09 |
|  | 4 | colorless | 7.1 | 100.0 | 0.46 | 0.09 |
| Comparative Example 1 | 0 | colorless | 7.2 | 102.5 | 0.05 | 0.05 |
|  | 1 | slightly light yellow | 7.1 | 87.9 | 7.91 | 3.81 |
|  | 2 | light yellow | 7.1 | 75.9 | 10.22 | 4.97 |
|  | 3 | yellow | 7.0 | 67.0 | 17.35 | 7.46 |
|  | 4 | dark yellow | 6.9 | 56.9 | 27.23 | 12.22 |
| Comparative Example 3 | 0 | colorless | 7.3 | 102.1 | 0.10 | 0.05 |
|  | 1 | light yellow | 7.2 | 92.9 | 6.15 | 3.01 |
|  | 2 | light yellow | 7.1 | 85.9 | 10.75 | 5.32 |
|  | 3 | yellow | 7.0 | 77.0 | 16.33 | 7.45 |
|  | 4 | Dark yellow | 6.9 | 65.9 | 25.11 | 10.28 |
| Comparative Example 4 | 0 | colorless | 7.4 | 102.0 | 0.08 | 0.04 |
|  | 1 | slightly light yellow | 7.2 | 94.9 | 7.91 | 2.61 |
|  | 2 | light yellow | 7.2 | 81.9 | 9.32 | 4.33 |
|  | 3 | yellow | 7.0 | 70.0 | 13.69 | 6.19 |
|  | 4 | Dark yellow | 6.9 | 58.5 | 26.56 | 11.84 |
| Comparative Example 5 | 0 | colorless | 7.3 | 101.5 | 0.12 | 0.05 |
|  | 1 | light yellow | 7.1 | 90.7 | 7.91 | 3.81 |
|  | 2 | Yellow | 7.1 | 79.3 | 11.22 | 4.97 |
|  | 3 | Dark yellow | 7.0 | 68.4 | 18.35 | 8.46 |
|  | 4 | Dark yellow | 6.8 | 56.9 | 31.23 | 12.22 |

As a result of the test, the formulation of Example 5 showed a slightly changed appearance after 1 month, but little changed drug content and the total related compounds degassing process and no color changes by addition of an antioxidant is the most stable aqueous solution formulation capable of being stored at room temperature.

[Test Example 3] Stress Stability Test for the Effect of Antioxidant Concentration and the Scale-Up The stability of formulations obtained in Examples 5, 7 and 10-15 was tested under a stressed condition (60° C./80% RH) for 4 weeks. The stability test results are shown in Table 8.

TABLE 8

| Item | Time (week) | Appearance | pH | Drug content (%) | Total related compounds (%) | Individual related compound (%) |
|---|---|---|---|---|---|---|
| Example 5 | 0 | colorless | 7.2 | 102.1 | 0.05 | 0.05 |
|  | 1 | colorless | 7.2 | 101.2 | 0.07 | 0.05 |
|  | 2 | slightly light yellow | 7.2 | 101.6 | 0.16 | 0.07 |
|  | 3 | slightly light yellow | 7.1 | 100.5 | 0.22 | 0.09 |
|  | 4 | light yellow | 7.1 | 101.0 | 0.29 | 0.12 |
| Example 7 | 0 | colorless | 7.3 | 102.5 | 0.10 | 0.05 |
|  | 1 | colorless | 7.2 | 101.9 | 0.23 | 0.08 |
|  | 2 | colorless | 7.2 | 101.6 | 0.31 | 0.08 |
|  | 3 | colorless | 7.1 | 101.5 | 0.35 | 0.09 |
|  | 4 | colorless | 7.1 | 101.5 | 0.36 | 0.09 |
| Example 10 | 0 | colorless | 7.4 | 101.2 | 0.06 | 0.06 |
|  | 1 | slightly light yellow | 7.3 | 101.5 | 0.17 | 0.07 |
|  | 2 | slightly light yellow | 7.2 | 101.1 | 0.26 | 0.11 |
|  | 3 | light yellow | 7.2 | 100.7 | 0.38 | 0.14 |
|  | 4 | light yellow | 7.0 | 100.8 | 0.42 | 0.16 |
| Example 11 | 0 | colorless | 7.3 | 101.7 | 0.11 | 0.06 |
|  | 1 | colorless | 7.2 | 101.2 | 0.12 | 0.06 |
|  | 2 | colorless | 7.2 | 101.3 | 0.13 | 0.07 |
|  | 3 | colorless | 7.2 | 100.9 | 0.15 | 0.06 |
|  | 4 | colorless | 7.1 | 100.2 | 0.20 | 0.07 |
| Example 12 | 0 | colorless | 7.2 | 101.5 | 0.11 | 0.06 |
|  | 1 | colorless | 7.2 | 100.7 | 0.12 | 0.06 |
|  | 2 | colorless | 7.1 | 100.6 | 0.15 | 0.06 |
|  | 3 | colorless | 7.0 | 101.0 | 0.21 | 0.07 |
|  | 4 | colorless | 6.9 | 100.5 | 0.20 | 0.06 |
| Example 13 | 0 | colorless | 7.3 | 101.1 | 0.11 | 0.06 |
|  | 1 | colorless | 7.2 | 101.3 | 0.12 | 0.06 |
|  | 2 | colorless | 7.1 | 100.4 | 0.21 | 0.06 |
|  | 3 | colorless | 7.0 | 100.2 | 0.24 | 0.07 |
|  | 4 | colorless | 6.9 | 100.2 | 0.25 | 0.06 |
| Example 14 | 0 | colorless | 7.3 | 102.1 | 0.11 | 0.06 |
|  | 1 | colorless | 7.2 | 101.2 | 0.23 | 0.07 |
|  | 2 | colorless | 7.0 | 100.5 | 0.29 | 0.07 |
|  | 3 | colorless | 7.0 | 100.4 | 0.34 | 0.07 |
|  | 4 | slightly light yellow | 6.9 | 100.0 | 0.38 | 0.08 |
| Example 15 | 0 | colorless | 7.3 | 101.8 | 0.09 | 0.05 |
|  | 1 | colorless | 7.2 | 100.9 | 0.25 | 0.06 |
|  | 2 | slightly light yellow | 7.1 | 100.2 | 0.33 | 0.07 |
|  | 3 | slightly light yellow | 7.0 | 99.9 | 0.39 | 0.08 |
|  | 4 | slightly light yellow | 6.8 | 100.3 | 0.43 | 0.09 |

As a result of the measurement, the 100 mg/ml formulation of Example 5 and the 1,000 mg/ml formulation of Example 10, both of which were prepared without antioxidant and subjected to freezing and degassing, showed nearly the same appearances and little drug content change, and contained total related compounds (standard: 1.5% or less) or individual related compounds (standard: 0.2% or less) in an amount of standard or lower.

The 100 mg/ml formulation of Example 7 and the 1,000 mg/ml formulation of Example 11, both of which were prepared with using an antioxidant (2.4 mg/ml of monothioglycerol) and subjected to freezing and degassing, showed nearly similar results of stress stability test. Thus, the freezing and vacuum degassing process according to the present invention could be applied for large-scale production as well as small-scale production.

As a result of testing the stability at various concentrations of antioxidants, the stability of the test formulations satisfied the standard regardless of the concentration of monothioglycerol in terms of the drug content and the content of related compounds. However, in terms of the color change, when the concentration of monothioglycerol was 0.1 mg/ml in Example 15, color was changed to slightly light yellow. Monothioglycerol, as an antioxidant, showed excellent stability without any change in color, and drug content and related compounds at a concentration of 0.24 mg/ml or more.

According to the test results, it is confirmed that the aqueous formulation with stability through the freezing and vacuum degassing process and no color changes with addition of a small amount of antioxidant is the most stable aqueous formulation that can be stored at room temperature. The freezing and vacuum degassing process can be scaled up, which can be used in a factory as well as in a laboratory.

[Test Example 4] Stress Stability Test with Various Kinds of Antioxidant

The stability of formulations obtained in Examples 7-9 prepared according to the composition of Table 2, was tested under a stressed condition (60° C./80% RH) for 3 months. The stability test results are shown in Table 9.

TABLE 9

| Item | Time (month) | Appearance | pH | Drug content (%) | Total related compounds (%) | Individual related compound (%) |
|---|---|---|---|---|---|---|
| Example 7 | 0 | colorless | 7.3 | 102.5 | 0.10 | 0.05 |
| | 1 | colorless | 7.1 | 101.5 | 0.36 | 0.09 |
| | 2 | colorless | 7.1 | 100.7 | 0.46 | 0.11 |
| | 3 | colorless | 7.0 | 100.1 | 0.54 | 0.12 |
| Example 8 | 0 | colorless | 7.4 | 102.0 | 0.04 | 0.04 |
| | 1 | light yellow | 7.1 | 101.0 | 0.34 | 0.12 |
| | 2 | yellow | 7.0 | 100.5 | 0.58 | 0.21 |
| | 3 | yellow | 6.8 | 99.8 | 0.84 | 0.29 |
| Example 9 | 0 | colorless | 7.3 | 101.5 | 0.14 | 0.07 |
| | 1 | colorless | 7.1 | 100.0 | 0.46 | 0.09 |
| | 2 | slightly light yellow | 7.0 | 100.2 | 0.55 | 0.10 |
| | 3 | slightly light yellow | 6.9 | 99.6 | 0.69 | 0.11 |

As a result, the three kinds of antioxidants satisfied the standard of the drug content and the content of related compounds. However, in terms of color, the formulation with sodium sulfide of Example 8 turned yellow color with lapse of time, and the formulation with acetylcysteine of Example 9 began to show slight color changes from 2 months. All the formulations satisfied the standard of related compounds, but the formulation using monothioglycerol showed a slightly better stability in terms of total related compounds. From the test results, it can be seen that monothioglycerol among various antioxidants is the most suitable antioxidant in terms of color changes and related compounds.

While the present invention has been particularly shown and described with reference to exemplary embodiments thereof, it is to be understood that the invention is not limited to the disclosed exemplary embodiments. Accordingly, the actual scope of the present invention will be defined by the appended claims and their equivalents.

The invention claimed is:

1. A method of preparing a pharmaceutical composition, comprising:
 (a) preparing a solution comprising pemetrexed or a pharmaceutically acceptable salt thereof, and an aqueous solvent in a container;
 (b) freezing the solution in the container to produce a frozen product; and
 (c) degassing the frozen product under reduced pressure to obtain a degassed and frozen product,
 wherein the degassed and frozen product comprises 95 to 100 parts by weight of the solvent per 100 parts by weight of the solvent contained in the solution of step (a), and
the steps of (b) and (c) are performed in a sealed chamber.

2. The method of claim 1, wherein the degassing in step (c) is performed to attain a dissolved oxygen concentration of 1.5 ppm or lower.

3. The method of claim 1, wherein the degassing in step (c) is performed for 12 hours or shorter.

4. The method of claim 1, wherein the solution of step (a) has not been degassed.

5. The method of claim 1, wherein the solution further comprises at least one selected from the group consisting of pharmaceutically acceptable excipients and pH adjusting agents.

6. The method of claim 5, wherein the excipient is mannitol, or the pH adjusting agent is hydrochloric acid, sodium hydroxide, or a mixture thereof.

7. The method of claim 1, wherein the solution further comprises an antioxidant.

8. The method of claim 7, wherein the antioxidant is monothioglycerol, sodium sulfite, acetylcysteine or a mixture thereof.

9. The method of claim 1, wherein the freezing in step (b) is performed at −20° C. or lower.

10. The method of claim 1, wherein the reduced pressure of step (c) is 2,000 mTorr or lower.

11. The method of claim 1, wherein the method further comprises a step of sealing the container or a step of filling the container with nitrogen followed by sealing, after step (c).

12. The method of claim 1, wherein the method further comprises thawing the degassed and frozen product, after step (c).

13. The method of claim 11, wherein the method further comprises thawing the degassed and frozen product, after the sealing the container.

* * * * *